US00PP08366P

United States Patent [19]

Bull

[11] Patent Number: Plant 8,366

[45] Date of Patent: Sep. 7, 1993

[54] IMPATIENS PLANT NAMED MATHILDE

[76] Inventor: Norbert Bull, Gärtnersiedlung 2, 2351 Gönnebek, Fed. Rep. of Germany

[21] Appl. No.: 803,467

[22] Filed: Dec. 6, 1991

[51] Int. Cl.[5] ..... A01H 5/00
[52] U.S. Cl. ..... Plt./87.6
[58] Field of Search ..... Plt./87.6

*Primary Examiner*—James R. Feyrer
*Attorney, Agent, or Firm*—Foley & Lardner

[57] ABSTRACT

An Impatiens plant named Mathilde, characterized by its large orange-red flowers, small very dark green foliage without variegation and with greyed-red under sides, compact growth habit, early flowering and floriferous habit, and by its flowers which stand strikingly above the foliage.

2 Drawing Sheets

The present invention relates to a new and distinctive cultivar of Impatiens plant, botanically known as Impatiens, and referred to be the cultivar name Mathilde. The new cultivar was developed by me through controlled breeding by crossing seed or female parent identified as Seedling No. 20 with male or pollen parent identified as Seedling No. 14. Both parents are unreleased and propriety lines.

Asexual reproduction of the new cultivar by the inventor by terminal or stem cuttings taken at Gönnebeck, Federal Republic of Germany has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. Orange-red flower color.
2. Compact growth habit.
3. Small, dark green foliage.
4. Very floriferous habit, with early flowering.
5. The flowers stand strikingly above the foliage and provide a good contrast with the foliage.
6. Suitable for pot plant, patio or bedding plant culture.

Mathilde can be compared to the cultivar Aurore. When so compared, Mathilde has an orange-red flower color, its foliage is smaller and darker, and there is no yellow variegation in the foliage.

The accompanying colored photographs illustrate the overall appearance of this cultivar, showing the colors as true as it is reasonably possible to obtain in a colored reproduction of this type.

The photo at the top of sheet 1 comprises a top perspective view of a potted plant of Mathilde.

The bottom photo on sheet 1 shows a single flower (top side), and top and bottom views of a typical leaf.

The photograph on sheet 2 shows the upper side and under side of typical flowers, a bud with attached spur, and the upper side and bottom side of typical leaves. Scales in centimeters are included to show the size of these parts.

The following is a detailed description of my new Impatiens cultivar based on plants produced under normal commercial practice at Gönnebek, Federal Republic of Germany.

Color references are made to the Royal Horticultural Society (R.H.S.) Colour Chart except where general terms of ordinary dictionary significance are used.

Parentage: Controlled cross between Bull Unnnamed Seedling No. 20×Bull Unnamed Seedling No. 14.

Propagation:

*Type cutting.*—Stem 15–20 mm long will grow to 4–5 cm in 20 days.

*Time to initiate roots.*—8 days at 22° C. summer.

*Time to initiate roots.*—10 days at 20° C. winter.

*Rooting habit.*—Very good.

Plant description:

Form.—Symmetrically mounded, self branching. Eight (8) weeks after sticking stem cuttings in 12 cm pots, plant is approximately 30 cm in diameter and 30 cm in height, measured from top of pot.

*Habit of growth.*—Compact growth habit.

*Foliage description.*—(1) Size: Small; length approximately 7 cm, width approximately 3 cm at point of maximum width. (2) Shape: Generally ovate, with acute to acuminate tip and rounded to acute base; see photos. (3) Margin: Mildy serrated. (4) Color: (a) Young foliage upper surface: Dark green, darker than RHS 139A. (b) Under surface: Greyed-purple 183B. (c) Mature foliage upper surface: Dark green, darker than RHS 139A. (d) Under surface: Greyed-purple 183B. (5) Veination: Red veins on upper side; under side veins (and under side color) are red (see photo). (6) Variegation: None.

Flowering description:

*Flowering habit.*—Flowers from leaf whorl in uniform manner.

*Natural flowering season.*—March until October.

*Flower buds.*—Typical; brown red in color.

*Flowers borne.*—On pedicels red-purple in color.

*Quantity of flowers.*—Very floriferous. Flowers both mask the crown and occur above the leaf canopy.

*Spur.*—Downwardly curved from base of calyx, approximately 4–5 cm in length and red-purple in color.

*Longevity.*—Flowers are long lasting and non-fading.

*Petals.*—Number of petals: Five (5). Shape: Generally heart-shaped (see photo). Color: Color very uniform. Upper surface: 44B. Under surface: Same as for top side, only slightly larger, approximately 44C-D. Size of flower: Large, approximately 6 cm. in diameter.

*Reproductive organs.*—Stamens: Five (5). Anthers: Hooded, orange-yellow in color. Pollen color: White. Stigma: Five in number, red in color.

Styles: Red in color. Ovary: 5 in number, size 3–5 mm., green in color.

Disease resistance: No disease problems noted to date.

I claim:

1. A new and distinct Impatiens plant named Mathilde, as illustrated and described.

* * * * *

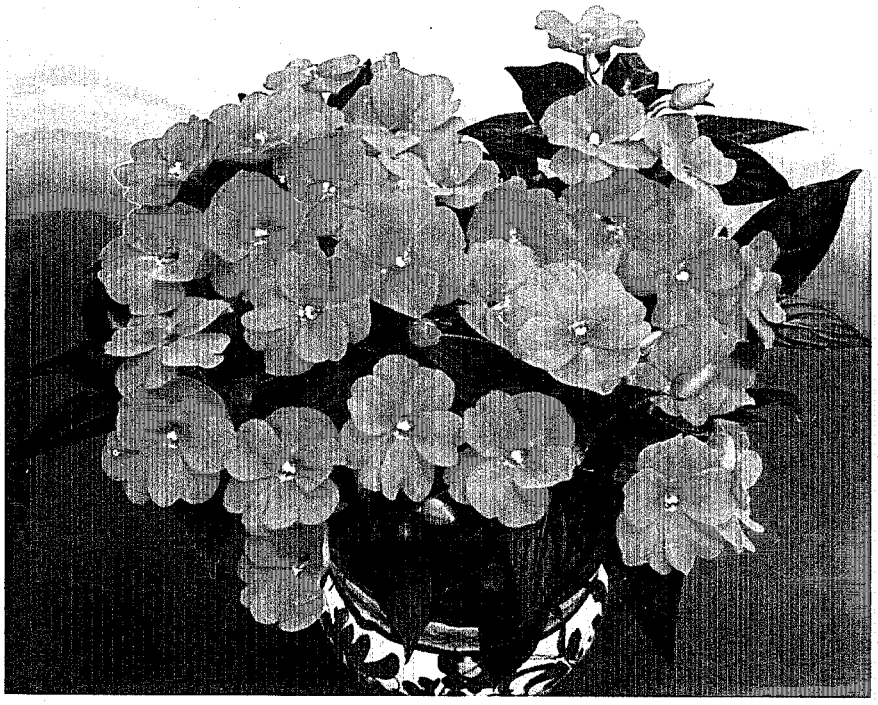
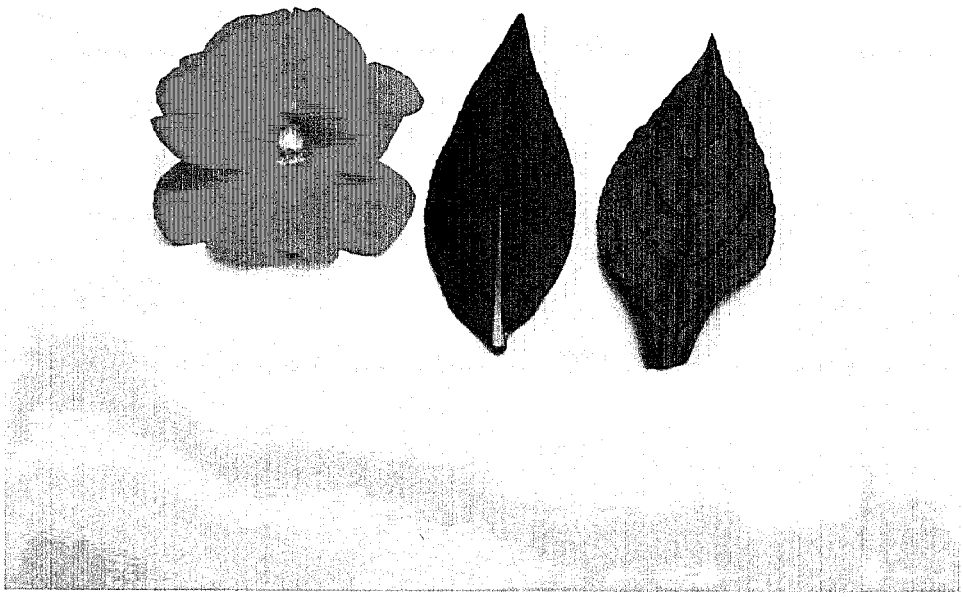

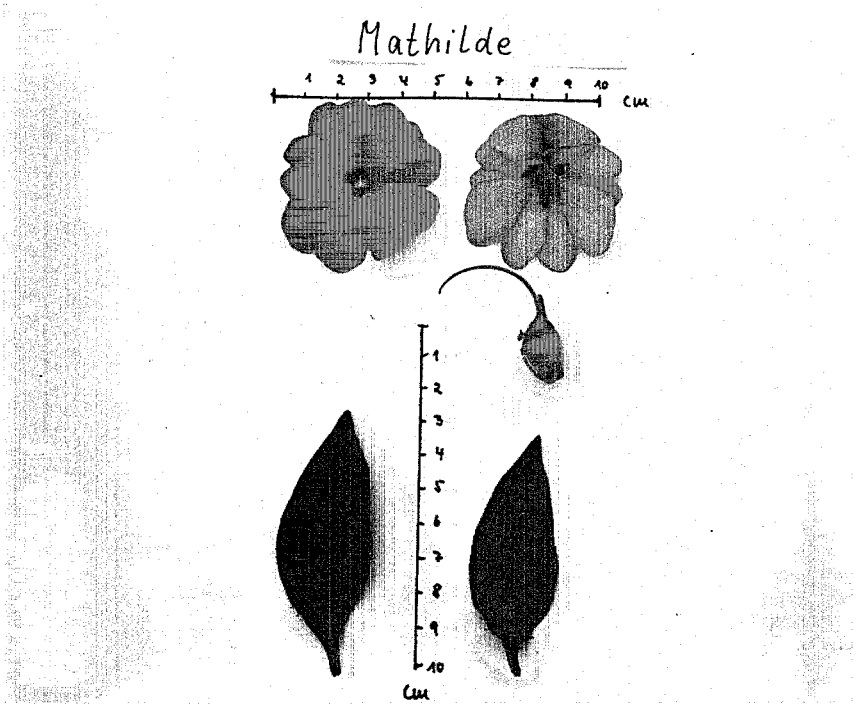
Mathilde
1 2 3 4 5 6 7 8 9 10
cm
1 2 3 4 5 6 7 8 9 10
cm